US008312033B1

(12) United States Patent
McMillan et al.

(10) Patent No.: US 8,312,033 B1
(45) Date of Patent: Nov. 13, 2012

(54) SYSTEMS AND METHODS FOR PROVIDING AN INTEGRATED IDENTIFIER

(75) Inventors: Helen McMillan, San Clemente, CA (US); John Lawrence Skurtovich, Jr., Anaheim, CA (US); Anita Kress, Newport Beach, CA (US); Timothy Sumida, Yorba Linda, CA (US); Michael Charles McVey, Mission Viejo, CA (US)

(73) Assignee: EXPERIAN MARKETING SOLUTIONS, Inc., Schaumburg, IL (US)

( * ) Notice: Subject to any disclaimer, the term of this patent is extended or adjusted under 35 U.S.C. 154(b) by 558 days.

(21) Appl. No.: 12/493,115

(22) Filed: Jun. 26, 2009

Related U.S. Application Data

(60) Provisional application No. 61/076,139, filed on Jun. 26, 2008.

(51) Int. Cl.
*G06F 17/00* (2006.01)

(52) U.S. Cl. ........................................ 707/758

(58) Field of Classification Search .................. None
See application file for complete search history.

(56) References Cited

U.S. PATENT DOCUMENTS

| | | |
|---|---|---|
| 5,590,038 A | 12/1996 | Pitroda |
| 5,640,577 A | 6/1997 | Scharmer |
| 5,659,731 A | 8/1997 | Gustafson |
| 5,666,528 A | 9/1997 | Thai |
| 5,692,107 A | 11/1997 | Simoudis et al. |
| 5,774,692 A | 6/1998 | Boyer et al. |
| 5,797,136 A | 8/1998 | Boyer et al. |
| 5,812,840 A | 9/1998 | Shwartz |
| 5,822,750 A | 10/1998 | Jou et al. |
| 5,822,751 A | 10/1998 | Gray et al. |
| 5,825,884 A | 10/1998 | Zdepski et al. |
| 5,844,218 A | 12/1998 | Kawan et al. |
| 5,881,131 A | 3/1999 | Farris et al. |
| 5,956,693 A | 9/1999 | Geerlings |
| 5,963,932 A | 10/1999 | Jakobsson et al. |

(Continued)

FOREIGN PATENT DOCUMENTS

JP 10-222559 8/1998

(Continued)

OTHER PUBLICATIONS

U.S. Appl. No. 12/705,489, filed Feb. 12, 2010, Bargoli et al.

(Continued)

*Primary Examiner* — Belix M Ortiz Ditren
(74) *Attorney, Agent, or Firm* — Knobbe, Martens, Olson & Bear, LLP

(57) ABSTRACT

Embodiments described herein provide systems and methods to streamline the mechanism by which data users access differently regulated data through the use of one or more integrated identifiers. The integrated identifiers lessen or eliminate the need to separately maintain one set of identifiers for regulated data and another set for non-regulated data. The methods and systems may be applicable in various credit and healthcare contexts where regulations over data use are prevalent. In one or more embodiments, a data user receives a unique integrated identifier for each of the data user's current or prospective customers, and the integrated identifiers can be used to persistently identify and track the customers over time and across applications that access regulated and/or non-regulated data. In the healthcare context, a healthcare provider may utilize a patient ID as the integrated identifier. To protect privacy, the integrated identifier may not include social security numbers or birthdates.

21 Claims, 5 Drawing Sheets

U.S. PATENT DOCUMENTS

| | | |
|---|---|---|
| 5,990,038 A | 11/1999 | Suga et al. |
| 6,038,551 A | 3/2000 | Barlow et al. |
| 6,070,147 A | 5/2000 | Harms et al. |
| 6,073,140 A | 6/2000 | Morgan et al. |
| 6,144,957 A | 11/2000 | Cohen et al. |
| 6,157,927 A | 12/2000 | Schaefer et al. |
| 6,223,171 B1 | 4/2001 | Chaudhuri et al. |
| 6,254,000 B1 | 7/2001 | Degen et al. |
| 6,304,869 B1 | 10/2001 | Moore et al. |
| 6,339,769 B1 | 1/2002 | Cochrane et al. |
| 6,366,903 B1 | 4/2002 | Agrawal et al. |
| 6,405,173 B1 | 6/2002 | Honarvar |
| 6,446,200 B1 | 9/2002 | Ball et al. |
| 6,457,012 B1 | 9/2002 | Jatkowski |
| 6,496,819 B1 | 12/2002 | Bello et al. |
| 6,523,022 B1 | 2/2003 | Hobbs |
| 6,523,041 B1 | 2/2003 | Morgan et al. |
| 6,574,623 B1 | 6/2003 | Leung et al. |
| 6,748,426 B1 | 6/2004 | Shaffer et al. |
| 6,766,327 B2 | 7/2004 | Morgan, Jr. et al. |
| 6,804,346 B1 | 10/2004 | Mewhinney |
| 6,850,895 B2 | 2/2005 | Brodersen et al. |
| 6,871,287 B1 | 3/2005 | Ellingson |
| 6,910,624 B1 | 6/2005 | Natsuno |
| 6,934,714 B2 | 8/2005 | Meinig |
| 6,983,379 B1 | 1/2006 | Spalink et al. |
| 6,983,478 B1 | 1/2006 | Grauch et al. |
| 6,985,887 B1 | 1/2006 | Sunstein et al. |
| 7,003,504 B1 | 2/2006 | Angus et al. |
| 7,028,001 B1 | 4/2006 | Muthuswamy et al. |
| 7,028,013 B2 | 4/2006 | Saeki |
| 7,028,052 B2 | 4/2006 | Chapman et al. |
| 7,035,855 B1 | 4/2006 | Kilger et al. |
| 7,047,251 B2 | 5/2006 | Reed et al. |
| 7,050,989 B1 | 5/2006 | Hurt et al. |
| 7,076,475 B2 | 7/2006 | Honarvar |
| 7,082,435 B1 | 7/2006 | Guzman et al. |
| 7,184,974 B2 | 2/2007 | Shishido |
| 7,185,016 B1 | 2/2007 | Rasmussen |
| 7,200,602 B2 | 4/2007 | Jonas |
| 7,209,895 B2 | 4/2007 | Kundtz et al. |
| 7,234,156 B2 | 6/2007 | French et al. |
| 7,246,740 B2 | 7/2007 | Swift et al. |
| 7,249,048 B1 | 7/2007 | O'Flaherty |
| 7,272,591 B1 | 9/2007 | Ghazal et al. |
| 7,277,900 B1 | 10/2007 | Ganesh et al. |
| 7,370,044 B2 | 5/2008 | Mulhern et al. |
| 7,373,335 B2 | 5/2008 | Cleghorn et al. |
| 7,403,942 B1 | 7/2008 | Bayliss |
| 7,421,442 B2 | 9/2008 | Gelb et al. |
| 7,424,439 B1 | 9/2008 | Fayyad et al. |
| 7,433,864 B2 | 10/2008 | Malik |
| 7,451,113 B1 | 11/2008 | Kasower |
| 7,458,508 B1 | 12/2008 | Shao et al. |
| 7,467,127 B1 | 12/2008 | Baccash et al. |
| 7,503,489 B2 | 3/2009 | Heffez |
| 7,509,117 B2 | 3/2009 | Yum |
| 7,512,221 B2 | 3/2009 | Toms |
| 7,529,698 B2 | 5/2009 | Joao |
| 7,536,346 B2 | 5/2009 | Aliffi et al. |
| 7,542,993 B2 | 6/2009 | Satterfield et al. |
| 7,548,886 B2 | 6/2009 | Kirkland et al. |
| 7,562,093 B2 | 7/2009 | Gelb et al. |
| 7,575,157 B2 | 8/2009 | Barnhardt et al. |
| 7,593,889 B2 | 9/2009 | Raines et al. |
| 7,596,512 B1 | 9/2009 | Raines et al. |
| 7,610,216 B1 | 10/2009 | May et al. |
| 7,620,596 B2 | 11/2009 | Knudson et al. |
| 7,623,844 B2 | 11/2009 | Herrmann et al. |
| 7,653,600 B2 | 1/2010 | Gustin |
| 7,672,833 B2 | 3/2010 | Blume et al. |
| 7,672,924 B1 | 3/2010 | Scheurich et al. |
| 7,672,926 B2 | 3/2010 | Ghazal et al. |
| 7,689,487 B1 | 3/2010 | Britto et al. |
| 7,689,505 B2 | 3/2010 | Kasower |
| 7,690,032 B1 | 3/2010 | Peirce |
| 7,708,190 B2 | 5/2010 | Brandt et al. |
| 7,747,559 B2 | 6/2010 | Leitner et al. |
| 7,752,236 B2 | 7/2010 | Williams et al. |
| 7,761,384 B2 | 7/2010 | Madhogarhia |
| 7,769,697 B2 | 8/2010 | Fieschi et al. |
| 7,793,835 B1 | 9/2010 | Coggeshall et al. |
| 7,797,252 B2 | 9/2010 | Rosskamm et al. |
| 7,841,004 B1 | 11/2010 | Balducci et al. |
| 7,849,014 B2 | 12/2010 | Erikson |
| 7,853,493 B2 | 12/2010 | DeBie et al. |
| 7,983,932 B2 | 7/2011 | Kane |
| 8,099,341 B2 | 1/2012 | Varghese |
| 2001/0011245 A1 | 8/2001 | Duhon |
| 2002/0010664 A1 | 1/2002 | Rabideau et al. |
| 2002/0026507 A1 | 2/2002 | Sears et al. |
| 2002/0052884 A1 | 5/2002 | Farber et al. |
| 2002/0069122 A1 | 6/2002 | Yun et al. |
| 2002/0077964 A1 | 6/2002 | Brody et al. |
| 2002/0099628 A1 | 7/2002 | Takaoka et al. |
| 2002/0103809 A1 | 8/2002 | Starzl et al. |
| 2002/0128962 A1 | 9/2002 | Kasower |
| 2002/0133504 A1 | 9/2002 | Vlahos et al. |
| 2002/0169747 A1 | 11/2002 | Chapman et al. |
| 2002/0198824 A1 | 12/2002 | Cook |
| 2003/0009418 A1 | 1/2003 | Green et al. |
| 2003/0009426 A1 | 1/2003 | Ruiz-Sanchez |
| 2003/0018549 A1 | 1/2003 | Fei et al. |
| 2003/0018578 A1 | 1/2003 | Schultz |
| 2003/0061163 A1 | 3/2003 | Durfield |
| 2003/0097380 A1 | 5/2003 | Mulhern et al. |
| 2003/0101344 A1 | 5/2003 | Wheeler et al. |
| 2003/0105728 A1 | 6/2003 | Yano et al. |
| 2003/0115133 A1 | 6/2003 | Bian |
| 2003/0171942 A1 | 9/2003 | Gaito |
| 2003/0195859 A1 | 10/2003 | Lawrence |
| 2003/0212654 A1 | 11/2003 | Harper et al. |
| 2003/0229892 A1 | 12/2003 | Sardera |
| 2004/0044628 A1 | 3/2004 | Mathew et al. |
| 2004/0111359 A1 | 6/2004 | Hudock |
| 2004/0117358 A1 | 6/2004 | Von Kaenel et al. |
| 2004/0153448 A1 | 8/2004 | Cheng et al. |
| 2004/0167793 A1 | 8/2004 | Masuoka et al. |
| 2004/0193891 A1 | 9/2004 | Ollila |
| 2004/0199456 A1 | 10/2004 | Flint et al. |
| 2004/0199789 A1 | 10/2004 | Shaw et al. |
| 2004/0220896 A1 | 11/2004 | Finlay et al. |
| 2004/0230527 A1 | 11/2004 | Hansen et al. |
| 2004/0230534 A1 | 11/2004 | McGough |
| 2005/0027983 A1 | 2/2005 | Klawon |
| 2005/0058262 A1 | 3/2005 | Timmins et al. |
| 2005/0137899 A1 | 6/2005 | Davies et al. |
| 2005/0154665 A1 | 7/2005 | Kerr |
| 2005/0177397 A1* | 8/2005 | Kane ................................ 705/2 |
| 2005/0187948 A1 | 8/2005 | Monitzer et al. |
| 2006/0020611 A1 | 1/2006 | Gilbert et al. |
| 2006/0041464 A1 | 2/2006 | Powers et al. |
| 2006/0059110 A1 | 3/2006 | Madhok et al. |
| 2006/0074986 A1 | 4/2006 | Mallalieu et al. |
| 2006/0074991 A1* | 4/2006 | Lussier et al. ................ 707/200 |
| 2006/0129481 A1 | 6/2006 | Bhatt et al. |
| 2006/0161435 A1 | 7/2006 | Atef et al. |
| 2006/0178971 A1 | 8/2006 | Owen et al. |
| 2006/0184585 A1 | 8/2006 | Grear et al. |
| 2006/0229943 A1 | 10/2006 | Mathias et al. |
| 2006/0229961 A1 | 10/2006 | Lyftogt et al. |
| 2006/0253358 A1 | 11/2006 | Delgrosso et al. |
| 2006/0262929 A1 | 11/2006 | Vatanen et al. |
| 2006/0271457 A1 | 11/2006 | Romain et al. |
| 2006/0282359 A1 | 12/2006 | Nobili et al. |
| 2007/0005508 A1 | 1/2007 | Chiang |
| 2007/0027816 A1 | 2/2007 | Writer |
| 2007/0067297 A1 | 3/2007 | Kublickis |
| 2007/0073889 A1 | 3/2007 | Morris |
| 2007/0078985 A1 | 4/2007 | Shao et al. |
| 2007/0083460 A1 | 4/2007 | Bachenheimer |

| | | | |
|---|---|---|---|
| 2007/0112667 | A1 | 5/2007 | Rucker |
| 2007/0124256 | A1 | 5/2007 | Crooks et al. |
| 2007/0156554 | A1 | 7/2007 | Nikoley et al. |
| 2007/0174186 | A1 | 7/2007 | Hokland |
| 2007/0174448 | A1 | 7/2007 | Ahuja et al. |
| 2007/0282730 | A1 | 12/2007 | Carpenter et al. |
| 2007/0288355 | A1 | 12/2007 | Roland et al. |
| 2008/0010206 | A1 | 1/2008 | Coleman |
| 2008/0010687 | A1 | 1/2008 | Gonen et al. |
| 2008/0059224 | A1 | 3/2008 | Schechter |
| 2008/0071682 | A1 | 3/2008 | Dominguez |
| 2008/0103972 | A1 | 5/2008 | Lanc |
| 2008/0175360 | A1 | 7/2008 | Schwarz et al. |
| 2008/0183480 | A1 | 7/2008 | Carlson et al. |
| 2008/0183504 | A1 | 7/2008 | Highley |
| 2008/0255992 | A1 | 10/2008 | Lin |
| 2008/0281737 | A1 | 11/2008 | Fajardo |
| 2008/0288299 | A1 | 11/2008 | Schultz |
| 2008/0320575 | A1 | 12/2008 | Gelb et al. |
| 2009/0006230 | A1 | 1/2009 | Lyda et al. |
| 2009/0024505 | A1 | 1/2009 | Patel et al. |
| 2009/0037332 | A1 | 2/2009 | Cheung et al. |
| 2009/0048877 | A1 | 2/2009 | Binns et al. |
| 2009/0106141 | A1 | 4/2009 | Becker |
| 2009/0106150 | A1 | 4/2009 | Pelegero et al. |
| 2009/0106846 | A1 | 4/2009 | Dupray et al. |
| 2009/0112650 | A1 | 4/2009 | Iwane |
| 2009/0126013 | A1 | 5/2009 | Atwood et al. |
| 2009/0177529 | A1 | 7/2009 | Hadi |
| 2009/0210241 | A1 | 8/2009 | Calloway |
| 2009/0260064 | A1 | 10/2009 | Mcdowell et al. |
| 2009/0307778 | A1 | 12/2009 | Mardikar |
| 2010/0043055 | A1 | 2/2010 | Baumgart |
| 2010/0094758 | A1 | 4/2010 | Chamberlain et al. |
| 2010/0114744 | A1 | 5/2010 | Gonen |
| 2010/0114776 | A1 | 5/2010 | Weller et al. |
| 2010/0145840 | A1 | 6/2010 | Kasower |
| 2010/0153278 | A1 | 6/2010 | Farsedakis |
| 2010/0179906 | A1 | 7/2010 | Hawkes |
| 2010/0185546 | A1 | 7/2010 | Pollard |
| 2010/0241535 | A1 | 9/2010 | Nightengale et al. |
| 2010/0280914 | A1 | 11/2010 | Carlson |
| 2011/0016042 | A1 | 1/2011 | Cho et al. |
| 2011/0035788 | A1 | 2/2011 | White et al. |
| 2012/0095927 | A1 | 4/2012 | Hirtenstein et al. |

FOREIGN PATENT DOCUMENTS

| | | |
|---|---|---|
| JP | 10-261009 | 9/1998 |
| JP | 2000-331068 | 11/2000 |
| JP | 2001-297141 | 10/2001 |
| JP | 2001-344463 | 12/2001 |
| JP | 2001-357256 | 12/2001 |
| JP | 2002-149778 | 5/2002 |
| JP | 2002-163498 | 6/2002 |
| JP | 2002-259753 | 9/2002 |
| JP | 2003-271851 | 9/2003 |
| JP | 2003-316881 | 11/2003 |
| KR | 10-2000-0036594 | 7/2000 |
| KR | 10-2000-0063995 | 11/2000 |
| KR | 10-2001-0016349 | 3/2001 |
| KR | 10-2001-0035145 | 5/2001 |
| KR | 10-2002-0007132 | 1/2002 |
| WO | WO 01/84281 | 11/2001 |
| WO | WO 2004/114160 | 12/2004 |

OTHER PUBLICATIONS

U.S. Appl. No. 12/705,511, filed Feb. 12, 2010, Bargoli et al.
"Intelligent Miner Applications Guide"; Chapter 4-7; pp. 33-132; IBM Corp., Apr. 2, 1999.
"Japan's JAAI system appraises used cars over internet", Asia Pulse Mar. 3, 2000.
"WashingtonPost.com and Cars.com launch comprehensive automotive web site for the Washington area". PR Newswire, Oct. 22, 1998.
Chores & Allowances. "Do Kids Have Credit Reports?" http://choresandallowances.blogspot.com/2007/10/do-kids-have-credit-reports.html Oct. 15, 2007 as printed May 31, 2011.
Elmasri et al., "Fundamentals of Database Systems, Third Edition (Excerpts),"pp. 253, 261, 268-70, 278-80, 585, 595, Jun. 2000.
Ettore, Paul Kahn on Exceptional Marketing. Management Review, vol. 38(11), Nov. 1994, pp. 48-51.
Gibbs, Adrienne; "Protecting Your Children from Identity Theft," http://www.creditcards.com/credit-card-news/identity-ID-theft-and-kids-children-1282.php Nov. 25, 2008 as printed Jul. 5, 2011.
ID Theft Assist, "Do You Know Where Your Child's Credit Is?" http://www.idtheftassist.com/pages/story14 Nov. 26, 2007, as printed May 31, 2011.
IDEON, Credit-Card Registry that Bellyflopped this Year, Is Drawing some Bottom-Fishers, The Wall Street Journal, Aug. 21, 1995, pp. C2.
LifeLock; "How can LifeLock protect my kids and family?," http//www.lifelock.com/lifelock-for-people/how-we-do-it/how-can-lifelock-protect-my-kids-and-family, accessed Mar. 14, 2008.
Loshin, Intelligent Enterprise: Better Insight for Business Decisions, "Value-Added Data: Merge Ahead", Feb. 9, 2000, vol. 3, No. 3, 5 pages.
Magid, Lawrence, J. , Business Tools: When Selecting an ASP Ensure Data Mobility, Los Angeles Times, Feb. 26, 2001, vol. C, Issue 4, pp. 3 pages, Los Angeles, CA.
Miller, Joe, "NADA used-car prices go online". Automotive News, Jun. 14, 1999, p. 36.
Ramaswamy, Vinita M., Identity-Theft Toolkit, The CPA Journal, Oct. 1, 2006, vol. 76, Issue 10, pp. 66 (5 pages).
Sawyers, Arlene "NADA to offer residual guide". Automotive News, May 22, 2000, p. 3.
Sax, Michael M., Data Collection and Privacy Protection : An International Perspective, Presentation: Managing Online Risk and Liability Conference, Aug. 31, 1999, pp. 58 pages.
Tao, Lixin; "Shifting Paradigms with the Application Service Provider Model"; Concordia University, Canada; IEEE; Oct. 2001.
Vamosi, Robert, "How to Handle ID Fraud's Youngest Victims," http://news.cnet.com/8301-10789_3-10105303-57.html, Nov. 21, 2008 as printed May 31, 2011.
Various Posts from the <p2p.wrox.com> Forums: http://web.archive.org/web/2005045221950/http://p2p.wrox.com/topic.asp?TOPIC_ID=6513, dated Nov. 15, 2003-Oct. 7, 2004.
Web Page posted at: http://web.archive.org/web20040805124909/http://www.oracle.com/technology/sample_codete/tech/pl_sql/htdocs/x/Case/start.htm, pp. 1 and 4 of the webs page posted on Jan. 7, 2003.
International Search Report and Written Opinion for Application No. PCT/US09/60393, (EXP.302VPC), dated Dec. 23, 2009.

* cited by examiner

SYSTEMS AND METHODS FOR PROVIDING AN INTEGRATED IDENTIFIER

CROSS-REFERENCE TO RELATED APPLICATIONS

This application claims the benefit of priority from U.S. Provisional Patent Application No. 61/076,139 filed on Jun. 26, 2008, entitled "Systems and Methods for Providing an Integrated Identifier," the entire contents of which are hereby incorporated herein by reference in their entirety. All publications and patent applications mentioned in this specification are herein incorporated by reference in their entirety to the same extent as if each individual publication or patent application was specifically and individually indicated to be incorporated by reference.

BACKGROUND

1. Field of the Invention

This disclosure generally relates to data processing, and more particularly to methods and systems for providing an integrated identifier for accessing differently regulated data.

2. Description of the Related Art

In the United States, the use of personal, credit, and financial data of consumers is regulated by at least the Fair Credit Reporting Act (FCRA) and the Gramm-Leach-Bliley Act (GLB). For example, under the FCRA, credit data may be used under certain permissible purposes, such as for account review purposes when a consumer already has an established account with a financial institution. In the healthcare field, the Health Insurance Portability and Accountability Act (HIPAA) governs the use of patient data. Organizations often need to manage customer or patient data including different types of data governed by different legal requirements, and thus face the challenge of complying with those requirements in the management of differently regulated data. The different legal requirements often lead to the use of parallel and sometimes duplicative data management systems and methods that increase the transfer of private or sensitive data across systems and networks. Besides increasing costs, the increased transfer also leads to increased security risks and exposes those organizations to liability for data privacy breaches.

SUMMARY OF THE DISCLOSURE

Embodiments described herein provide data management systems and methods for accessing, providing, and/or managing differently regulated data. The data management systems and methods may streamline the mechanism by which data users access both regulated and non-regulated data through the use of one or more integrated identifiers. An identifier may be an alphanumeric string and/or a database record key. It may be encrypted or in clear text. In one or more embodiments an identifier does not contain any personally identifiable information. Other embodiments include systems and methods that allow for the integration of a Customer Data Integration (CDI) solution with an account review service through the use of one or more integrated identifiers.

In one embodiment, the integrated identifiers are managed by a reconciliation system that (1) reconciles various identifiers in use in regulated and non-regulated data sources into the single integrated identifiers and (2) resolve the integrated identifiers and translate them back to the various identifiers for accessing regulated and non-regulated data sources. The reconciliation and resolution logic takes into account the potential mismatches in the data records concerning the same individual consumers or businesses, including the various possibilities when there is not a one-to-one correspondence. The reconciliation system accomplishes its tasks while maintaining compliance with various legal requirements concerning regulated data. Therefore, the systems and methods may lessen or eliminate the need to separately maintain one set of identifiers for regulated data and another set for non-regulated data. The methods and systems may be applicable in various credit and healthcare contexts where regulations over data use are prevalent.

In one embodiment, a data user receives a unique integrated data identifier for each of the data user's current or prospective customers, which may be individual consumers or businesses. The integrated data identifiers can be used by the data user to persistently identify and track the customers over time and across software applications. The integrated data identifier can also be accurately and consistently translated within a data provider (such as a credit bureau) to link and deliver corresponding consumer and business data within the varying asset databases and services maintained by the data provider. In the healthcare context, a healthcare provider or an insurer may utilize a patient ID as the integrated identifier. In one or more embodiments, to protect privacy, the integrated identifier does not include personal information such as social security numbers or birthdates.

BRIEF DESCRIPTION OF THE DRAWINGS

Specific embodiments will now be described with reference to the following drawings.

DESCRIPTION OF CERTAIN EMBODIMENTS

Figure 1:
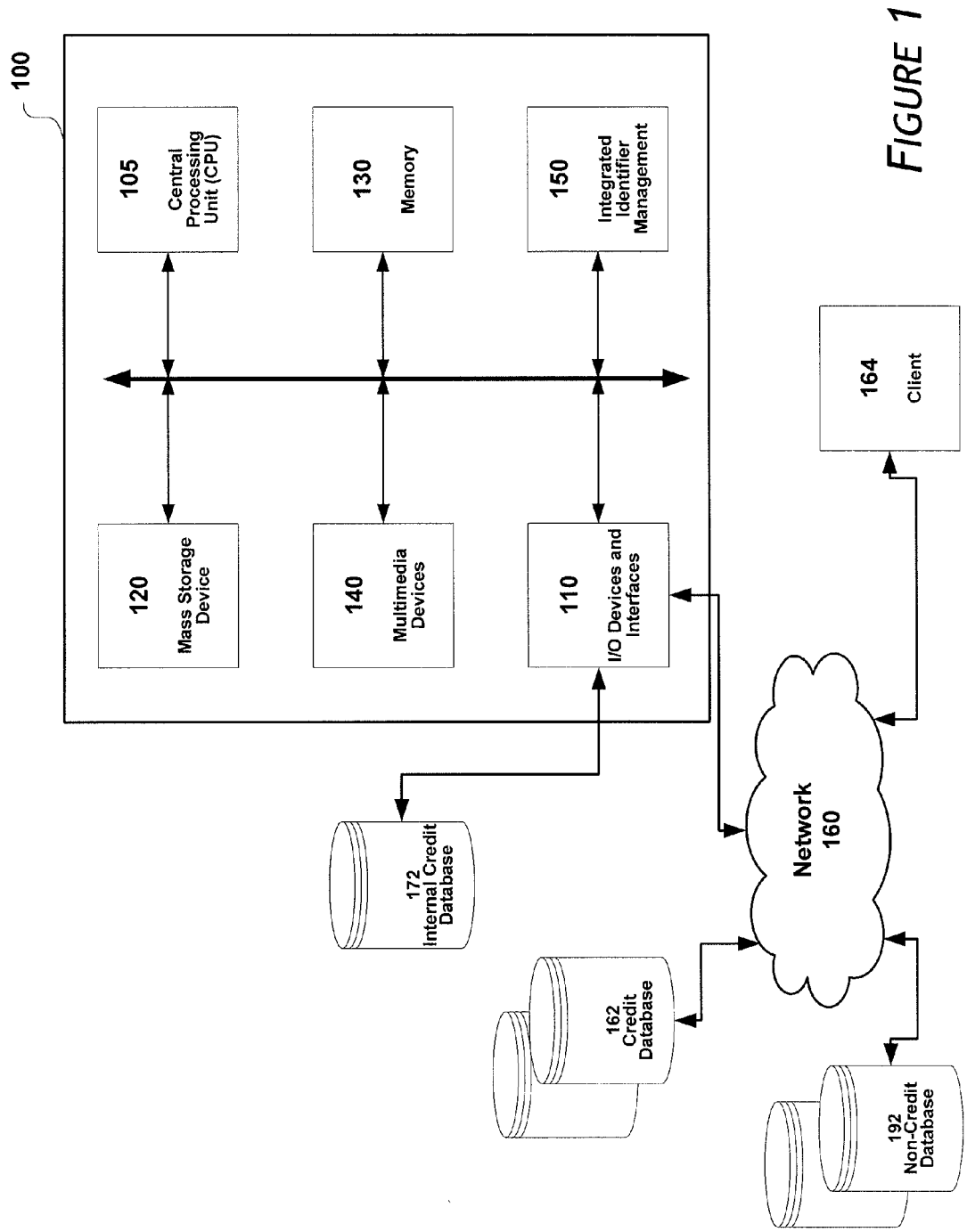
FIG. 1 is a block diagram of an integrated identifier reconciliation system according to one embodiment.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions described herein.

Various companies store information about their customers in a collection of systems and databases. Customer data integration ("CDI") solutions, such as Experian's Truvue solution, synchronize records across multiple business units and databases to deliver a more complete, consistent and accurate view of customers over time. One advantage of a CDI solution may be that it can integrate thousands of reliable and verifiable data sources (collectively referred to as "customer data") into one or more large intelligent reference databases. With links to thousands of contributors of reliable and verifiable data, information may be updated continually. When combined with vast name and address history stored by a credit bureau, these links may give a data user entity that uses the CDI the ability to accurately identify and link comprehensive data to their customers.

Many data users, such as credit card issuers, banks, utility companies, and other commercial entities, for example, need to manage customer data. In addition, these data users often access regulated data such as credit data, sometimes in conjunction with one or more access operations involving non-regulated customer data. For example, a card issuer may wish to use non-regulated customer data for marketing purposes and regulated credit data for processing new credit applications. One difficulty these data users encounter is the divergent methods of access that are needed due to the different regulations restricting the use of certain data. Other data users in fields such as healthcare may also face the same challenge in their data management practices. For example, a healthcare provider or an insurer may face one set of legal requirements with regard to patient data (e.g., HIPPA) and another set of requirements with regard to the use of credit data related to those patients (e.g., FCRA). For example, a pharmacy may need to manage three types of regulated data: medical data, insurance data, and credit data.

Typically the legal requirements limit use of data to certain permissible purposes, and as a result the different legal requirements often lead to the use of parallel and sometimes duplicative data management systems and methods that cannot be cross-referenced. For example, if a credit card company purchased a marketing list (usually non-regulated) containing prospective customers and wished to check the list against its current account holders in a regulated credit database, legal requirements may require the company to assign identifiers to the prospective customers on the marketing list, assign the same identifiers to its list of current account holders, and then compare the two lists. However, according to certain embodiments discussed herein, the credit card company may provide the list of prospective customers to a system that will automatically resolve, in a compliance manner, to the proper integrated identifiers that also correspond to the identifiers used in the regulated credit database.

Embodiments described herein provide data management systems and methods for accessing, providing, and/or managing differently regulated data. The data management systems and methods streamline the mechanism by which data users access both regulated and non-regulated data through the use of one or more integrated identifiers. An identifier may be an alphanumeric string and/or a database record key. It may be encrypted or in clear text. In one or more embodiments an identifier does not contain any personally identifiable information. Other embodiments include systems and methods that allow for the integration of a Customer Data Integration (CDI) solution with an account review service through the use of one or more integrated identifiers. Embodiments may also ensure that the use of these regulated data in the integrated environment is still consistent with the legal requirements concerning use. In one embodiment, the systems and methods are configured to comply with various federal and state legislations.

In addition, the systems and methods may minimize or reduce the need to transfer consumer private data to the data provider, for example, for the purpose of conducting the account review services or other services. The systems and methods may also help identify other service opportunities for improving efficiency and/or quality, as well as other services that can utilize the integrated identifier.

Integrated Identifier

Embodiments employ one or more integrated identifiers for the interface and delivery of multiple products and services derived from various data sources, including but not limited to those from a data provider such as a credit bureau.

In one embodiment, a data user (e.g., a client of the credit bureau or a client of a data provider) can receive a unique integrated identifier for each of the data user's current or prospective customers, which may be a consumer or a business. Other data providers may include insurance companies, healthcare providers, etc. The unique integrated identifiers can be used by the data user to persistently identify and track both regulated and/or non-regulated data associated with its customers over time and across applications. In one embodiment, a credit processing software application may interface with a data provider, such as a credit bureau, that delivers consumer and business data from within the regulated and/or non-regulated databases and services maintained by the data provider. In the healthcare context, a healthcare provider or an insurer may utilize a patient ID as the integrated identifier. In one or more embodiments, to protect privacy, the integrated identifier does not include personal information such as social security numbers or birthdates. In one embodiment, the integrated identifier is from a data provider, and in one embodiment the integrated identifier is from a data user. The integrated identifier may be an existing identifier in either the data user or the data provider's database, or a new identifier.

In one embodiment, existing marketing data services solution infrastructure and/or customer database solutions may be used as a platform for building and maintaining a cross reference between corresponding consumers on a truth database (e.g., Experian Marketing Services' Truth Database) and a credit database maintained by a credit bureau (e.g., Experian's File One Database).

One or more embodiments are configured so that the use of designed integrated identifiers does not change the regulatory status of any of the credit bureau's core asset database(s). In one embodiment, the integrated identifier includes safeguards that will prohibit it from being incorrectly used or referenced within the data provider's and within the data user's systems and applications. In one embodiment used in the credit context, the system prevents the integrated identifier from being used as an alternative identifier for defining a consumer associated with a credit account when reporting account updates to a credit bureau's primary credit database. Instead, updates need to comply with consumer credit reporting standards, such as the "Metro2" standard defined by the Associated Credit Bureaus, Inc (ACB).

Computing System

In some embodiments, the systems, computer clients and/or servers described herein take the form of a computing system as shown in FIG. 1. FIG. 1 is a block diagram showing an embodiment in which computing system 100 is in communication with a network 160 and various systems are also in communication with the network 160. The computing system 100 may be used to implement systems and methods described herein. For example, the computing system 100 may be configured to receive financial and demographic information regarding individuals and generate reports and/or alerts for one or more clients. Although the description provided herein refers to individuals, consumers, or customers, the terms "individual," "consumer," and "customer" should be interpreted to include applicants, or groups of individuals or customers or applicants, such as, for example, married couples or domestic partners, organizations, groups, and business entities.

The computing system 100 includes, for example, a server or personal computer that is IBM, Macintosh, or Linux/Unix compatible. In one embodiment, the computing system 100 comprises a server, a laptop computer, a cell phone, a personal digital assistant, a kiosk, or an audio player, for example. In one embodiment, the exemplary computing system 100 includes one or more central processing unit ("CPU") 105, which may include a conventional microprocessor. The computing system 100 further includes one or more memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standard based bus system. In different embodiments, the standard based bus system could be Peripheral Component Interconnect ("PCI"), Microchannel, Small Computer System Interface ("SCSI"), Industrial Standard Architecture ("ISA") and Extended ISA ("EISA") architectures, for example. In addition, the functionality provided for in the components and modules of computing system 100 may be combined into fewer components and modules or further separated into additional components and modules.

The computing system 100 is generally controlled and coordinated by operating system software, such as Windows 95, Windows 98, Windows NT, Windows 2000, Windows XP, Windows Vista, Windows 7, Unix, Linux, SunOS, Solaris, or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, I/O services, and provide a user interface, such as a graphical user interface ("GUI"), among other things.

The exemplary computing system 100 includes one or more commonly available input/output (I/O) devices and interfaces 110, such as a keyboard, mouse, touchpad, and printer. In one embodiment, the I/O devices and interfaces 110 include one or more display device, such as a monitor, that allows the visual presentation of data to a user. More particularly, a display device provides for the presentation of GUIs, application software data, and multimedia presentations, for example. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is electronically coupled to a network 160, which comprises one or more of a LAN, WAN, or the Internet, for example, via a wired, wireless, or combination of wired and wireless, communication link 115. The network 160 communicates with various computing devices and/or other electronic devices via wired or wireless communication links.

According to FIG. 1, information is provided to computing system 100 over the network 160 from one or more data sources including, for example, credit databases 162. The information supplied by the various data sources may include credit data, demographic data, application information, product terms, accounts receivable data, and financial statements, for example. In addition to the devices that are illustrated in FIG. 1, the network 160 may communicate with other data sources or other computing devices. In addition, the data sources may include one or more internal and/or external data sources. In some embodiments, one or more of the databases or data sources may be implemented using a relational database, such as Sybase, Oracle, CodeBase and Microsoft® SQL Server as well as other types of data structures such as, for example, a flat file database, an entity-relationship database, and object-oriented database, and/or a record-based database.

In addition to supplying data, client 164 may further request information from the computing system 100. For example, the client 164 may request data related to a consumer or a group of consumers. Such a request may include consumer information identifying the consumer(s) for which information is desired. The client may also provide updates to the one or more databases shown in the figure. For example, the client 164 may send, to the computing system 100, new account information when a customer opens a new credit card account so that one or more credit or non-credit databases reflects the customer's new account.

The I/O devices and interfaces 110 further provide a communication interface to an internal credit database 172. In the embodiment of FIG. 1, the computing system 100 is coupled to a secured network 161, such as a secured LAN, for example. The system 100 may communicate with the internal credit database 172 through a secured network (not shown), for example. In some embodiments, the internal credit database 172 is configured to communicate with additional computing devices over the network 160 or some other network, such as a LAN, WAN, and/or the Internet via a wired, wireless, or combination of wired and wireless, communication link. In certain embodiments, the client 164 may have access to the internal credit database 172 through the network 160.

In the embodiment of FIG. 1, the computing system 100 also includes an integrated identifier management module 150 that may be executed by the CPU 105. This module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In the embodiment shown in FIG. 1, the computing system 100 is configured to execute integrated identifier management module 150, among others, in order to reconcile identifiers and personal identification numbers associated with respective customers among the internal credit database 172, credit databases 162, and/or non-credit databases 192. The reconciliation process associate disparate identifiers to one or more integrated identifiers for the same customers, so that different data sources can be accessed with the integrated identifiers. The various reconciliation methods will be further described below. In some embodiments, the integrated identifier management module 150 may be configured to access and/or obtain data from internal credit database 172, credit databases 162, non-credit databases 192, or a combination of internal credit database 172, credit databases 162 and non-credit databases 192.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Providing Access to Non-Regulated and Regulated Data Sources

Figure 2A:
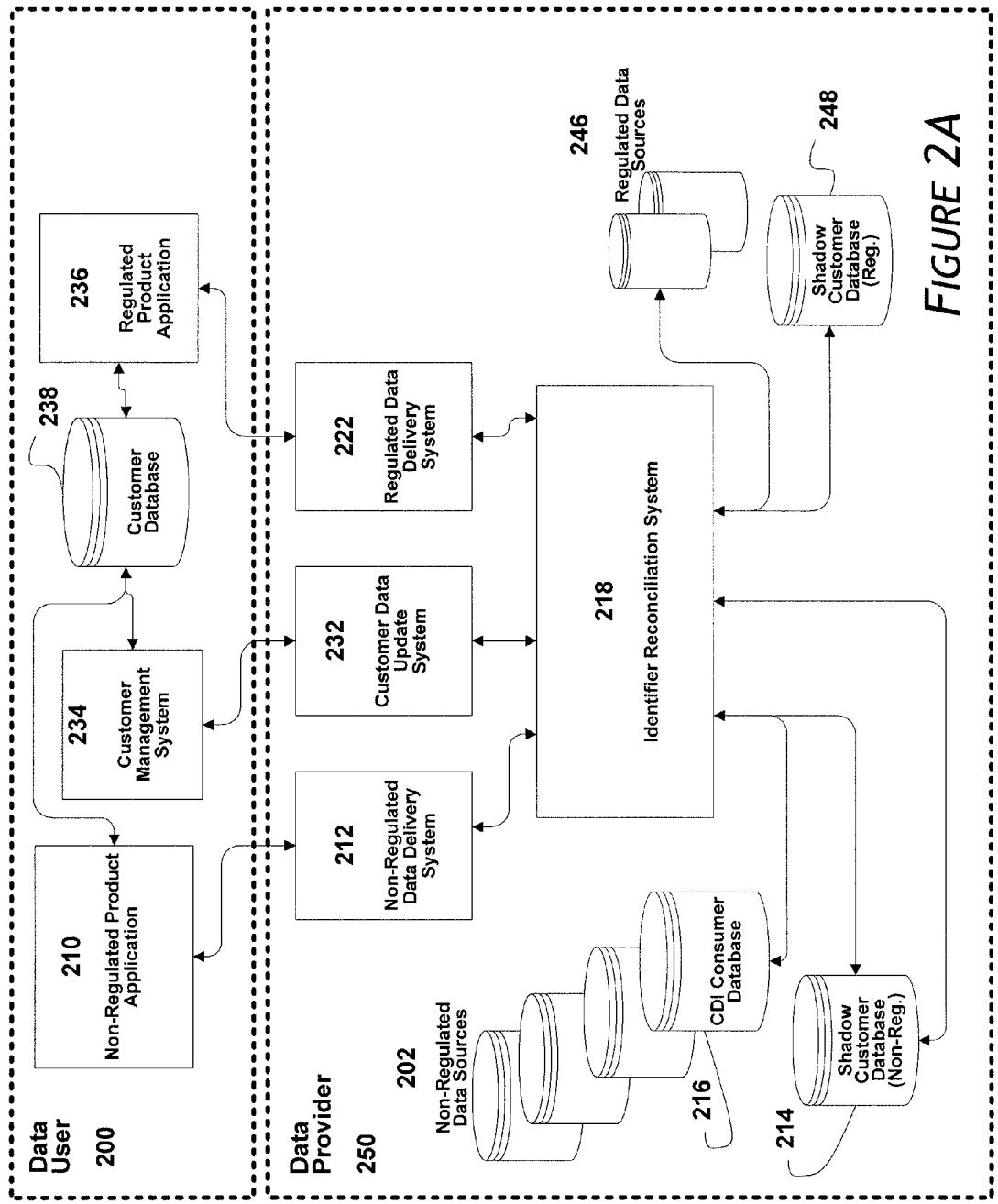
FIG. 2A is a block diagram showing a system for providing and utilizing integrated identifiers according to one embodiment.

FIG. 2A is a block diagram showing a system for providing and utilizing integrated identifiers according to one embodiment. In the embodiment of FIG. 2A, a data user 200 can access various data sources provided by one or more data provider 250 (e.g., a credit bureau), including non-regulated data 202 and regulated data 246. As depicted in the figure, the data user 200 may operate a Non-Regulated Product Application 210, a Regulated Product Application 236, and/or a Customer Management System 234. The data user 200 may use the integrated identifiers throughout its applications and systems to refer to individuals or businesses, and use the same integrated identifiers to access regulated and non-regulated data provided by the data provider 250. In one or more embodiments, the reconciliation mechanisms employed by the data provider 250 eliminate the need for the data user 200 to maintain separate identifiers for regulated and non-regulated data for the same individuals or businesses.

Non-Regulated Data Sources

In one embodiment, the Non-Regulated Product Application 210 is tasked with accessing non-regulated data. For example, if the data user 200 is a credit card company, the Non-Regulated Product Application 210 may handle the tasks of gathering data to find prospective customers, verifying information relating those prospective customers, and pre-qualifying selected prospective customers for credit card offers. In one or more of these tasks, the Non-Regulated Product Application 210 accesses a Non-Regulated Data Delivery System 212, which serves as an interface to a number of databases containing non-regulated data sources 202 from which data may be accessed, acquired and/or verified. In one or more embodiments, the Non-Regulated Data Delivery System 212 is operated by the data provider 250.

Among non-regulated data sources 202 may be a CDI Consumer Database 216, which may serve as the primary data source for the Non-Regulated Data Delivery System 212 in one embodiment. The CDI Consumer Database 216 may also serve as the primary database in which the data user 200 correlates its customer data with other sources of non-regulated data. In one embodiment, CDI Consumer Database 216 stores a history of data points for the individual consumers identified. The data points may be retrieved from qualified data sources so that the CDI Consumer Database 216 provides consistent and accurate information about consumers. For example, the Non-Regulated Product Application 210 may send information of a prospective customer to the Non-Regulated Data Delivery System 212 to request a lookup of the prospective customer in one or more of the non-regulated data sources 202. The Non-Regulated Data Delivery System 212 may attempt to locate the prospective customer in the CDI Consumer Database 216 using the received information. The Non-Regulated Data Delivery System 212 may then return to the Non-Regulated Product Application 210 the non-regulated data identifier(s) of the matched record(s) within the CDI Consumer Database 216, along with other data from data sources 202 that are associated with the particular prospective customer. In one embodiment, the returned data include the matched record for the customer in the CDI Consumer Database 216, the ID (the identifier) for the matched record in the CDI Consumer Database 216, and/or other associated data records for that customer from other data sources 202. If no matches are found, a new non-regulated data identifier may be assigned and returned to the Non-Regulated Product Application 210. If multiple matches are found, the Identifier Reconciliation System 218 follows a reconciliation process that will be further described in detail below. In one embodiment, Identifier Reconciliation System 218 may be implemented as the computing system 100.

In one embodiment, the returned non-regulated data identifier serves as the integrated identifier through which other applications and systems of the data user 200 may access both regulated and non-regulated data. In some embodiments, the integrated identifiers can also access multiple sources of non-regulated data. In one embodiment, the returned integrated identifiers are saved in a Customer Database 238. In one embodiment, one integrated identifier is returned for each individual customer. With reference to flow chart in FIG. 2B, which is discussed in further detail below, the same returned identifiers are saved in a Non-Regulated Shadow Customer Database 214 in block 260 to facilitate the process of identifier reconciliation. In one embodiment, the Non-Regulated Shadow Customer Database 214 mirrors at least a portion of the records stored in the Customer Database 238 and links the records to the assigned integrated identifiers. An entry in the Non-Regulated Customer Shadow Database 214 may include a pairing of the customer's record in the customer database 238 with the non-regulated identifier that has been returned the customer.

Regulated Data Sources

Embodiments also provide methods and systems that enable data users to access regulated data sources with the identifiers that have been assigned as the integrated identifiers, which may also be used for accessing non-regulated data. In one embodiment, a Regulated Data Delivery System 222 provides an interface for accessing regulated data sources 246. For example, the Regulated Data Delivery System 222 may receive queries from the Regulated Product Application 236 to obtain credit reports for credit applicants. In one or more embodiments, the Regulated Data Delivery System 222 implements one or more rules to ensure that access to the regulated data sources complies with applicable legal requirements.

In one embodiment, the Regulated Product Application 236 may forward to the Regulated Data Delivery System 222 an identifier that has been assigned as the integrated identified and previously returned by the Non-Regulated Data Delivery System 212, along with other query data (e.g., name, Social Security Number) for the retrieval of regulated data. The Regulated Data Delivery System 222, may then access the regulated data sources, locate the records and the associated regulated data identifiers that match the query data, and return them to the Regulated Product Application 236.

Figure 2B:
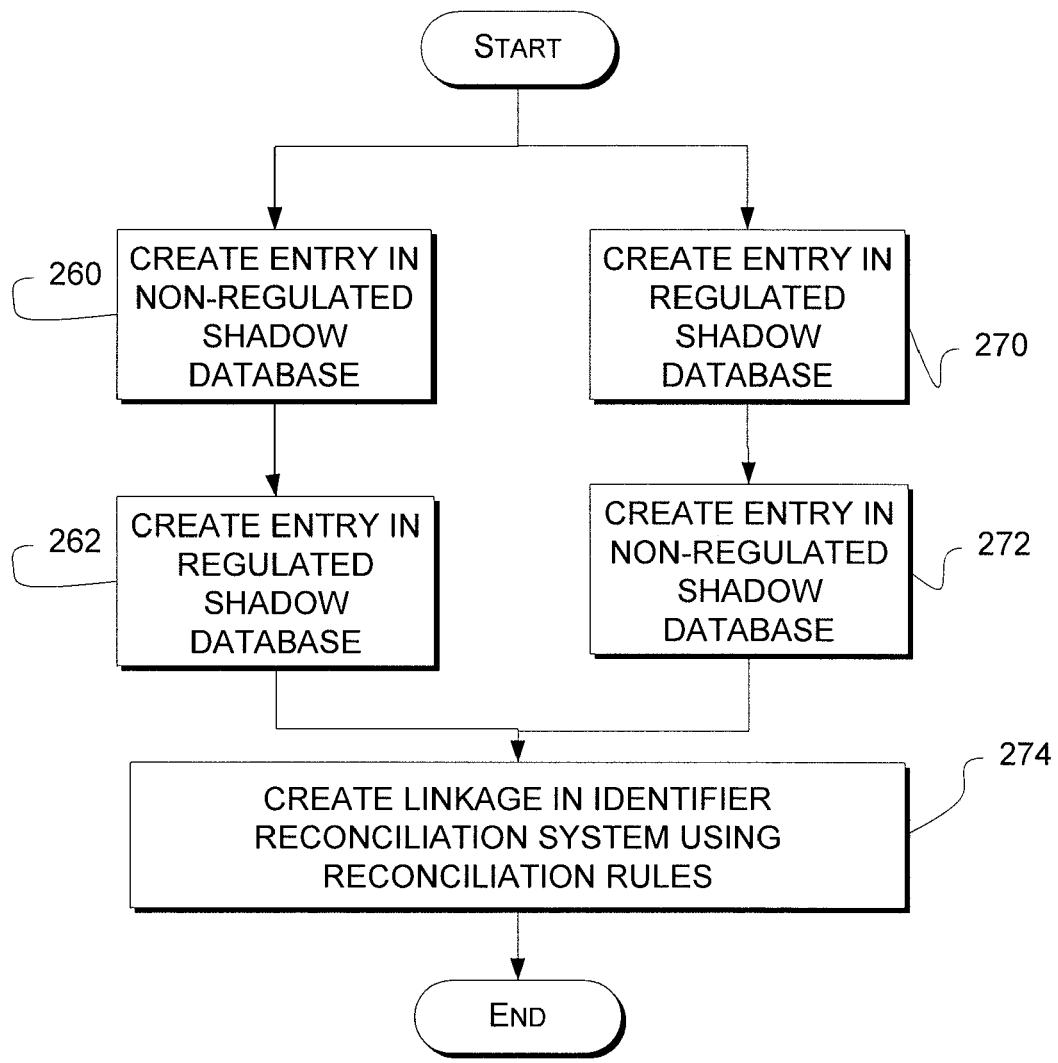
FIG. 2B is a flow diagram showing a method for reconciling integrated identifiers according to one embodiment.

FIG. 2B is a flow diagram showing a method for reconciling integrated identifiers according to one embodiment. In the embodiment of FIG. 2B, the lookup process may trigger (1) as shown in block 262, the creation of an entry in the Regulated Customer Shadow Database 248, and (2) as shown in block 274, the creation, within the Identifier Reconciliation System 218, of a linkage between the previously created entry in the Regulated Customer Shadow Database 218 and the corresponding entry in the Regulated Customer Shadow Database 248. In one embodiment, the Regulated Shadow Customer Database 248 mirrors at least a portion of the records stored in the Customer Database 238 and links the records to the located regulated data identifiers. In one embodiment, the linkage is created using a set of reconciliation rules as further described below. An entry in the Regulated Customer Shadow Database 248 may include a pairing of the customer's record in the customer database 238 with the regulated identifier for the customer. In one embodiment, the Regulated Customer Shadow Database 248 and the Non-Regulated Customer Shadow Database 214 may be implemented as distinct tables or data structures within one database.

As shown also by blocks 270 and 272 in FIG. 2B, the process of creating the linkage may occur in a different order if the data user accesses regulated data first and subsequently accesses non-regulated data. In one embodiment, this order is an alternative method of execution to that which is depicted in blocks 260 and 262. In this situation, a lookup of the non-regulated data source may be needed in block 270 to retrieve a non-regulated data identifier and provide it to the data user 200. In another embodiment, blocks 270 and 272 may take place concurrently with blocks 260 and 262, or before or after blocks 260 and 262.

Identifier Reconciliation

In one embodiment, the Identifier Reconciliation System 218 includes the integrated identifier management module 150 (from FIG. 1) that reconciles identifiers for regulated and non-regulated data. As described above, the Non-Regulated Shadow Database 214 and the Regulated Shadow Database 248 each keeps a shadow copy of the records in the Customer Database 238 with different identifiers. Hence, data accesses by the data user to various data sources with the integrated identifiers need to be reconciled or resolved properly. In one embodiment, the non-regulated data identifiers are used as the integrated identifiers, which are used in the Customer Database 238 and the Non-Regulated Shadow Database 214. In one embodiment, the regulated data identifiers are used in the Regulated Shadow Database 248.

In one embodiment, the reconciliation module reconciles identifiers for regulated and non-regulated data. In one embodiment, the integrated identifier management module 150 may follow one or more business rules in its reconciliation process. The rules account for the possibility that there may be one-to-one, many-to-one, or many-to-many correspondences between records in non-regulated data sources and those in regulated data sources. The rules may include one or more of the following:

(A) For the condition where a regulated data identifier (e.g., a unique PIN assigned by a credit bureau) is matched to a non-regulated data identifier (which may be used as the integrated identifier as described above), the link between the regulated data identifier and the non-regulated data identifier may be created and maintained in a data linkage table without additional processing.

(B) For the condition where multiple regulated data identifiers are matched to one non-regulated data identifier, the following rules may be used. (1) If the regulated identifiers are deemed indicative of duplicate data records in a regulated database, the Identifier Reconciliation System 218 may initiate an inquiry to the data user to trigger a merge of the multiple duplicative regulated data identifiers in the regulated database. (2) However, if data management mechanism associated with the regulated database does not allow such a merge, then new non-regulated identifiers may be created for each unique regulated data identifier.

(C) For the condition where multiple non-regulated data identifiers are matched to one regulated data identifier, the multiple non-regulated data identifiers may be merged into one inquiry at the CDI Consumer Database 216 in one embodiment and a resolution process is then executed to identify a resulting non-regulated data identifier that will be assigned to the credit data identifier.

(D) For the condition where a non-regulated data identifier does not match any regulated data identifier, an error message may be output for manual research & resolution. In some embodiments, a regulated data identifier may be created for the non-regulated data identifier.

(E) For the condition where a regulated data identifier does not match any non-regulated data identifiers, a new non-regulated data identifier may be created for the individual identified by the regulated data identifier. The non-regulated data identifier may be marked as private data, so that it is visible only to the data user that is requesting the reconciliation.

(F) For the condition where multiple regulated data identifiers match multiple non-regulated data identifiers, in one embodiment, the system is configured to follow the above rules regarding many-to-one correspondences.

It is to be understood that the above rules are implemented in one or more embodiments, for example, in embodiments where FCRA and/or GLB regulated data are used. Other embodiments, such as those in the healthcare context, may use different rules. In addition, the reconciliation rules used in various embodiments of the invention may be updated to ensure continued compliance with changing laws and regulations. In one or more embodiments, the Identifier Reconciliation System 218 is configured to periodically check a data source that provides a set of updated rules. Finally, although the examples above describe regulated and non-regulated data, the integrated identifiers are not so limited may be used to provide access to differently-regulated data, e.g. two or more sources of differently regulated data.

Identifier Resolution

With the linkage in place, the Identifier Reconciliation System 218 provides identifier resolution so that the data user 200 can access both regulated and non-regulated data with the integrated identifier. For example, the data user 200 may operate a Customer Management System 234 that handles tasks such as account creation and account maintenance. The Customer Management System 234 interacts with a Customer Data Update System 232, which manages transactions by also utilizing the Identifier Reconciliation System 218.

Figure 2C:
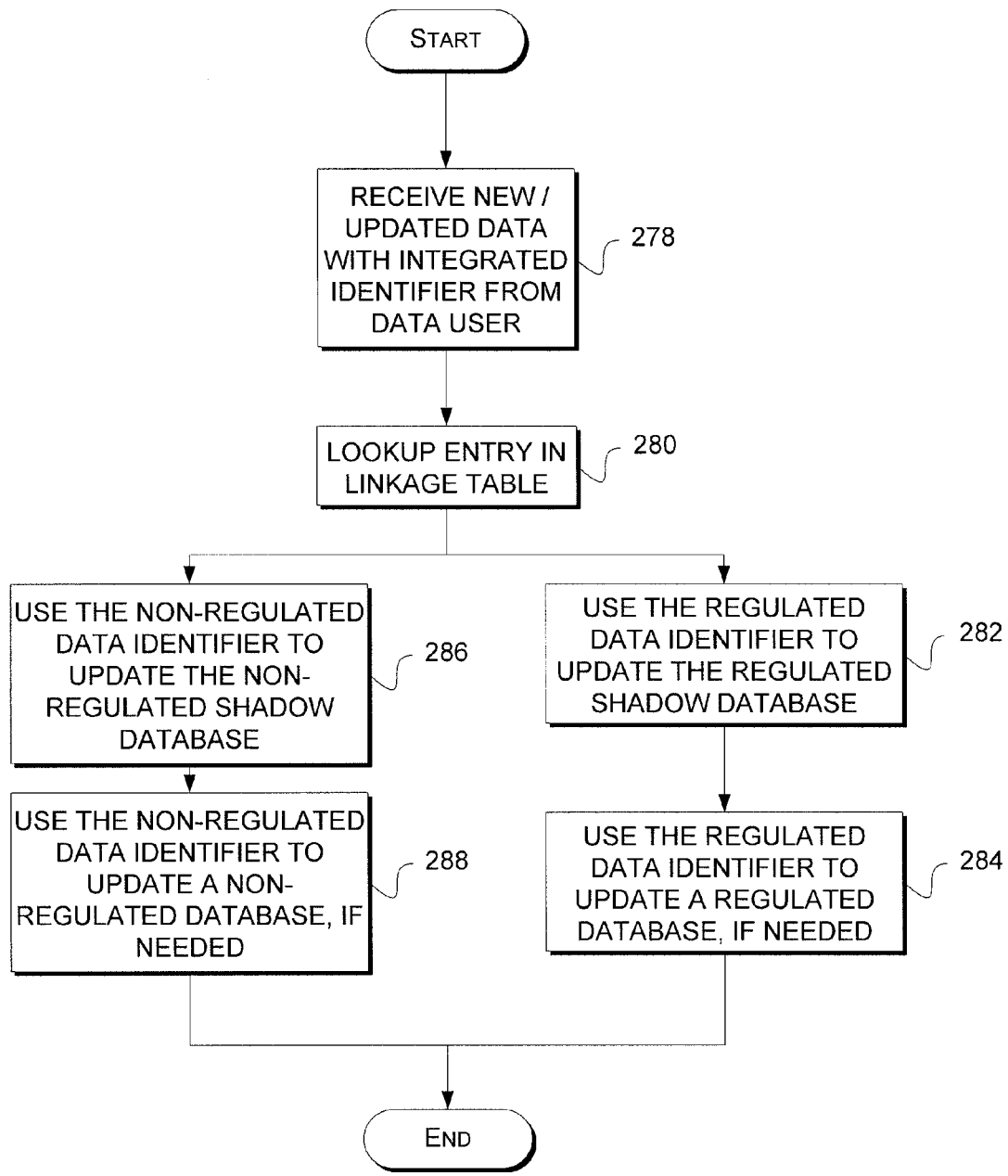
FIG. 2C is a flow diagram showing a method for resolving integrated identifiers according to one embodiment.

FIG. 2C is a flow diagram showing a method for resolving integrated identifiers according to one embodiment. An example of an identifier resolution process is described below with reference to FIG. 2C. Such an example may entail the creation of a new customer account. The Customer Management System 234 may create the new account in the Customer Database 238 with the integrated identifier. Then, in block 278, the Customer Data Update System 232 may receive, from the Customer Management System 234, the new account information along with the integrated identifier associated with the new customer, both of which may be passed to the Identifier Reconciliation System 218. The Identifier Reconciliation System 218 may then look up the appropriate entries in the linkage table in block 280. The lookup may resolve to identifiers usable for either an update to the Non-Regulated Shadow Customer Database 214 and/or the Regulated Shadow Customer Database 248, along with actual updates to the appropriate regulated or non-regulated data sources (blocks 282, 284, 286, and 288).

In one or more embodiments, systems 212, 222, and 232 may be part of the Identifier Reconciliation System 218, which serves as a central access point of any data applications of the data user. In addition, although the examples described above describe accessing data in individual transactions, systems 212, 222, and 232 in one or more embodiments may be configured to support batch processing where data records are processed in accordance with the mechanisms described above in batches.

Description of Other Embodiments Applied to Specific Contexts

Figure 3:
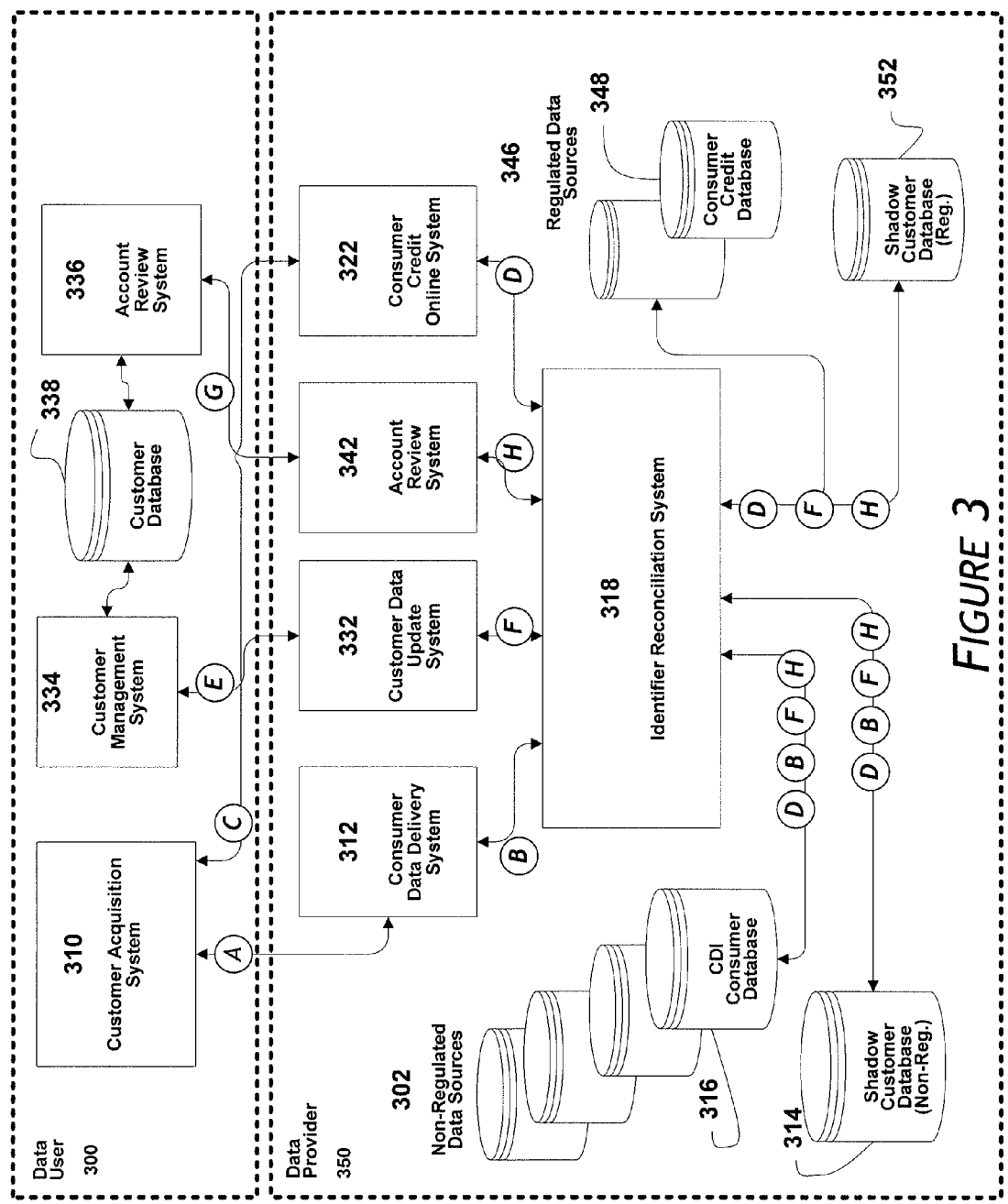
FIG. 3 is a block diagram showing a system for providing and utilizing integrated identifiers in accordance with another embodiment.

FIG. 3 shows an embodiment as applied in the credit context. A data user 300 can access various databases provided by a data provider 350, for example, a credit bureau, including non-regulated data 302 and regulated data 346 through the use of integrated identifiers. Non-regulated data 302 may include CDI data and other related data, while regulated data 346 may include credit data, including credit data used for account review purposes. As depicted in the figure, the data user may operate a Customer Acquisition System 310, which handles the task of acquiring new customers. For example, if the data user is a credit card company, Customer Acquisition System 310 may handle the tasks of gathering data to locate prospective customers, verifying information relating those prospective customers, and qualifying selected prospective customers for credit card offers. In another example, if the data user is a utility company, the Customer Acquisition System 310 may be used to determine a customer's eligibility to receive services. In the healthcare setting, the Customer Acquisition System 310 may be used by a healthcare provider to admit new patients.

In one or more of these tasks, the Customer Acquisition System 310 may access a Consumer Data Delivery System 312, which serves as an interface to a number of databases containing non-regulated data sources 302 from which data may be acquired and/or verified. In one or more embodiments, the Consumer Data Delivery System 312 is operated by the data provider 350.

Non-Regulated Data Sources

Among database sources 302 may be a CDI Consumer Database 316, which may serve as the primary data source for the Consumer Data Delivery System 312. The CDI Consumer Database 316 may also serve as the primary database in which the data user 300 correlates its customer data with other sources of data. For example, as shown in process "A," the Customer Acquisition System 310 may, upon the receipt of information of for a prospective customer "Customer A" (e.g., name and address), send the received prospective customer information to the Consumer Data Delivery System 312 to request a lookup of "Customer A" in the non-regulated data sources 302. In one embodiment, as shown in process "B," the Consumer Data Delivery System 312 attempts to locate "Customer A" in the CDI Consumer Database 316 using the received information, and return, to the Customer Acquisition System 310, the customer data ID(s) of the matched record(s) for "Customer A" within the CDI Consumer Database 316, along with other data from data sources 302 that are associated with "Customer A."

Non-regulated data sources 302 may include a government database such as one managed by the Office of Foreign Assets Control (OFAC) and a fraud database such as the National Fraud Database. For example, if the data user 300 is a credit card company, the returned information from the CDI Consumer Database and/or other related non-regulated data sources may contain information related to the prospective customer that can help the credit card company assess the type of products in which the prospective customer may be interested, and/or whether the prospective customer may be a high fraud risk. In one embodiment, the customer data ID from the CDI Consumer Database 316 is returned to the data user 300 and saved in the customer database 338. The customer data ID for "Customer A" is then used as the integrated identifier to access both regulated and non-regulated information. In the example of "Customer A," the result may be that he or she becomes pre-approved based on the information received. Both the Non-Regulated Shadow Customer Database 314 and the Customer Database 338 may be updated to reflect that "Customer A" has been pre-approved and that an integrated identifier has been assigned to him or her.

In one or more embodiments, a list of prospective customers may be provided by the Customer Acquisition System 310 to the Consumer Data Delivery System 312, which in turn may locate data records for the list of prospective customers from among the non-regulated data sources 302. In addition, the Consumer Data Delivery System 312 may also query the Non-Regulated Shadow Customer Database 314 to check if any of the prospective customers are already existing customers of the data user 300.

Although a number of modules depicted include the term "consumer," embodiments provide the same data management capability for data users that manage business customers. Thus, in one or more embodiments, the Consumer Data Delivery System 312 may access a CDI Business Database instead of or in addition to the CDI Consumer Database 316.

Regulated Data Sources

Embodiments also provide methods and systems for data users to access regulated data sources. As shown in process "C," the Consumer Credit Online System 322 may receive credit queries from the Customer Acquisition System 310. In one embodiment, the Consumer Credit Online System 322 interfaces with regulated data sources 346 such as a Consumer Credit Database 348. Using the "Customer A" example, after receiving a pre-approval notice, "Customer A" may submit a credit application to the data user 300. The Consumer Credit Online System 322 may then receive queries from the Customer Acquisition System 310 to obtain credit reports for "Customer A," under the permissible purpose of determining credit-worthiness, for example. In the process "D," "Customer A's" credit reports are obtained from a Consumer Credit Database 348. The retrieved reports are then returned to the data user 300.

The data user 300 may also operate a Customer Management System 334 that handles tasks such as account creation and account maintenance. Tracking along with the example, if the returned credit reports are satisfactory, "Customer A" may be approved for a new account and the Customer Management System 334 may handle the creation of the account. As shown in process "E," the Customer Management System 334 may send "Customer A's" new account information along with the assigned integrated identifier to a Customer Update System 332, which manages additions and updates in one embodiment via an Identifier Reconciliation System 318. The Customer Management System 334 may forward the integrated identifier in the process "F" to the Identifier Reconciliation System 318, and the identifier reconciliation process as shown in FIG. 2B may be triggered so that the Non-Regulated Shadow Customer Database 314, the Regulated Shadow Customer Database 352, and/or other databases are updated. The Customer Data Update System may also receive updates from the Customer Management System 334 reflecting changes in the Customer Database 338. In one embodiment, the updates are sent with the integrated identifiers, which are resolved in accordance to the resolution process shown in FIGS. 2A and 2C, so that the appropriate shadow databases and/or regulated or non-regulated data sources are updated. In one embodiment, the updates can be processed in by transaction or in a batch mode.

The data user 300 may also operate an Account Review System 336 that forwards customer information along with the integrated identifiers to the counterpart Account Review System 342 of the data provider 350, as shown in process "G." For example, if the data user 300 is a credit card company, the information may include account numbers. In one embodiment, the account numbers and identifiers are then sent to the Identifier Reconciliation System 318, as shown in process "H." The Identifier Reconciliation System 318 may then resolve to the proper regulated identifiers based on its linkage table and then access the Consumer Credit Database 348 to obtain data records needed for the account review. The results are then returned to the Account Review System 336.

CONCLUSION

All of the methods described herein may be performed and fully automated by a computer system. The computer system may, in some cases, be composed by multiple distinct computers or computing devices (e.g., physical servers, workstations, storage arrays, etc.) that communicate and interoperate over a network to perform the described functions. Each such computing device typically includes a processor (or multiple processors) that executes program instructions stored in a memory. The results of the disclosed methods may be persistently stored by transforming physical storage devices, such as solid state memory chips and/or magnetic disks, into a different state.

In addition, all of the methods/processes described above may be embodied in, and fully automated via, software code modules executed by one or more general purpose computers. The code module may be stored in any type of computer-readable medium or other computer storage device. Some or all of the methods may alternatively be embodied in specialized computer hardware. As will be apparent, the features, and attributes of the specific embodiments disclosed above may be combined in different ways to form additional embodiments, all of which are fall within the scope of the present disclosure. Although this disclosure has been described in terms of certain preferred embodiments and applications, other embodiments and applications that are apparent to those of ordinary skill in the art, including embodiments which do not provide all of the features and advantages set forth herein, are also within the scope of this disclosure. Accordingly, the scope of the disclosure is intended to be defined only by reference to the appended claims.

The invention claimed is:

1. A system for providing integrated identifiers comprising:
    a first database that stores a first plurality of records comprising regulated data, the first plurality of records accessible by a plurality of regulated data identifiers;
    a second database that stores a second plurality of records comprising non-regulated data, the second plurality of records accessible by a plurality of non-regulated data identifiers; and
    a computing device in communication with the first database and the second database, comprising:
        an integrated identifier management module, the management module configured to:
            intermittently reconcile a selected plurality of non-regulated data identifiers and a selected plurality of regulated data identifiers by:
                determining a correlation between data associated with certain non-regulated data identifiers and data associated with certain regulated data identifiers; and
                associating regulated data identifiers and non-regulated data identifiers having a determined correlation therebetween with respective integrated identifiers; and
        an application module for accepting data requests to access data in the first or second database, whereby the records of the first database and the second database are accessible by the respective integrated identifiers.

2. The system of claim 1 wherein the integrated identifier management module is further configured to associate the selected non-regulated data identifiers with the selected regulated data identifiers by determining whether for each selected non-regulated data identifier, there is a corresponding regulated data identifier.

3. The system of claim 2 wherein the integrated identifier management module is further configured to associate the selected non-regulated data identifiers with the selected regulated data identifiers by triggering a merge of multiple selected regulated data identifiers into one regulated data identifier in response to determining that the multiple selected regulated data identifiers correspond to a single selected non-regulated data identifier.

4. The system of claim 1 wherein the integrated identifier management module is further configured to store correspondences between the integrated identifiers and respective regulated data identifiers and non-regulated data identifiers having the determined correlation therebetween.

5. The system of claim 4 further comprising:
    a first shadow database that stores a plurality of records comprising customer data stored in a customer database, the records accessible by the plurality of regulated data identifiers; and
    a second shadow database that stores a plurality of records comprising customer data stored in the customer database, the records accessible by the plurality of non-regulated data identifiers.

6. The system of claim 1 wherein the first database stores credit data.

7. The system of claim 1 wherein the second database stores marketing data.

8. The system of claim 1 wherein the first database stores medical data.

9. The system of claim 1 wherein the first database and the second database store data records associated with individuals.

10. The system of claim 1 wherein the first database and the second database store data records associated with businesses.

11. A system for providing integrated identifiers comprising:
    a first database that stores a first plurality of records comprising data regulated under a first set of legal requirements, the first plurality of records accessible by a plurality of first regulated data identifiers;
    a second database that stores a second plurality of records comprising data regulated under a second set of legal requirements, the second plurality of records accessible by a plurality of second regulated data identifiers; and
    a computing device in communication with the first database and the second database, comprising:
        an integrated identifier management module, the management module configured to:
            reconcile a selected plurality of first regulated data identifiers and a selected plurality of second regulated data identifiers by:

determining a correlation between certain first regulated data identifiers and certain second regulated data identifiers; and associating groups of first regulated and second regulated data identifiers with respective integrated identifiers;

an application module for accepting data requests to access data in the first or second database, whereby the records of the first database and the second database are accessible using respective integrated identifiers.

12. The system of claim 11 wherein the first database and the second database store data records associated with individuals.

13. The system of claim 11 wherein the first database and the second database store data records associated with businesses.

14. A method for providing integrated identifiers, the method configured for execution by a computing device having one or more processors, the method comprising:

accessing a first data structure storing a first plurality of records comprising regulated data, the first plurality of records accessible by a corresponding plurality of regulated data identifiers;

accessing a second data structure storing a second plurality of records comprising non-regulated data, the second plurality of records accessible by a corresponding plurality of non-regulated data identifiers;

intermittently reconciling the plurality of non-regulated data identifiers and the plurality of regulated data identifiers by:

determining a correlation between data associated with certain non-regulated data identifiers and data associated with certain regulated data identifiers; and associating regulated data identifiers and non-regulated data identifiers with respective integrated identifiers in response to determined correlations therebetween.

15. The method of claim 14 further comprising identifying correlations between the non-regulated data identifiers and the regulated data identifiers by determining whether for each non-regulated data identifier there is a corresponding regulated data identifier.

16. The method of claim 14 further comprising identifying correlations between the non-regulated data identifiers and the selected regulated data identifiers by triggering a merge of multiple selected regulated data identifiers into one regulated data identifier in response to determining that the multiple selected regulated data identifiers correspond to a single individual or business.

17. The method of claim 14 further comprising storing correspondences between integrated identifiers and the regulated data identifiers and non-regulated data identifies with a determined correlation therebetween.

18. A non-transitory computer-readable medium having stored thereon instructions that, in response to execution by a computer system, cause the computer system to:

access a first data structure storing a first plurality of records comprising regulated data, the first plurality of records accessible by a corresponding plurality of regulated data identifiers;

access a second data structure storing a second plurality of records comprising non-regulated data, the second plurality of records accessible by a corresponding plurality of non-regulated data identifiers;

intermittently reconcile the plurality of non-regulated data identifiers and the plurality of regulated data identifiers by:

determining a correlation between data associated with certain non-regulated data identifiers and data associated with certain regulated data identifiers; and associating regulated data identifiers and non-regulated data identifiers with respective integrated identifiers in response to determined correlations therebetween.

19. The non-transitory computer-readable medium of claim 18, having stored thereon instructions that, when executed by the computer system, cause the computer system to associate the selected non-regulated data identifiers with the selected regulated data identifiers by determining whether for each selected non-regulated data identifier, there is a corresponding regulated data identifier.

20. The non-transitory computer-readable medium of claim 18, having stored thereon instructions that, when executed by the computer system, cause the computer system to associate the selected non-regulated data identifiers with the selected regulated data identifiers by triggering a merge of multiple selected regulated data identifiers into one regulated data identifier in response to determining that the multiple selected regulated data identifiers correspond to a single selected non-regulated data identifier.

21. A system for providing integrated identifiers comprising:

a first data structure that stores a first plurality of records comprising regulated data, the first plurality of records associated with a corresponding plurality of regulated data identifiers;

a second data structure that stores a second plurality of records comprising non-regulated data, the second plurality of records associated with a corresponding plurality of non-regulated data identifiers; and a computing device in communication with the first data structure and the second data structure, the computing device comprising:

an integrated identifier module configured to:

intermittently reconcile a selected plurality of the non-regulated data identifiers and a selected plurality of the regulated data identifiers by:

determining a correlation between data in a record associated with a first non-regulated data identifier and data in a record associated with a first regulated data identifier; and associating both the first non-regulated data identifier and the first regulated data identifier with a first integrated identifier; and an application module for accepting data requests to access data in the first data structure and the second data structure, whereby the record associated with the first non-regulated data identifier and the record associated with the first regulated data identifier are accessible using the first integrated identifier.

* * * * *

UNITED STATES PATENT AND TRADEMARK OFFICE
CERTIFICATE OF CORRECTION

PATENT NO. : 8,312,033 B1
APPLICATION NO. : 12/493115
DATED : November 13, 2012
INVENTOR(S) : McMillan et al.

Page 1 of 1

It is certified that error appears in the above-identified patent and that said Letters Patent is hereby corrected as shown below:

On Title Page 3, Item (56) References Cited:

In column 2 at line 3, Under Other Publications, change "Chapter" to --Chapters--.

In column 2 at line 38, Under Other Publications, change "Arlene" to --Arlena--.

In the Claims:

In column 15 at line 52 (approx.), In Claim 17, change "identifies" to --identifiers--.

Signed and Sealed this
Twenty-eighth Day of May, 2013

Teresa Stanek Rea
*Acting Director of the United States Patent and Trademark Office*